United States Patent [19]

Sangokoya et al.

[11] Patent Number: 5,066,631

[45] Date of Patent: Nov. 19, 1991

[54] HYDROCARBON SOLUTIONS OF ALKYLALUMINOXANE COMPOUNDS

[75] Inventors: Samuel A. Sangokoya; Milham S. Howie; Todd A. Trumbo, all of Baton Rouge, La.

[73] Assignee: Ethyl Corporation, Richmond, Va.

[21] Appl. No.: 598,117

[22] Filed: Oct. 16, 1990

[51] Int. Cl.$^5$ .............................................. C08F 4/52
[52] U.S. Cl. .................................... 502/152; 502/103; 502/110; 502/117
[58] Field of Search ................ 502/152, 103, 110, 117

[56] References Cited

U.S. PATENT DOCUMENTS 4,794,096 12/1988 Ewen .................................. 502/117

FOREIGN PATENT DOCUMENTS 1-258686 10/1989 Japan .

OTHER PUBLICATIONS

Kioka et al, Jap. Pat. App. 63-87717, *Patent Abstracts of Japan*, vol. 14, No. 14, (Jan. 12, 1990).

*Primary Examiner*—Patrick P. Garvin
*Assistant Examiner*—Brent M. Peebles
*Attorney, Agent, or Firm*—David M. Bunnell

[57] ABSTRACT

A hydrocarbon solvent solution of alkylaluminoxane comprises a hydrocarbon solvent having dissolved therein methylaluminoxane and an effective amount to solubilize the methylaluminoxane in the solvent of tri-n-alkylaluminum wherein the alkyl groups each contain at least two carbon atoms.

19 Claims, No Drawings

HYDROCARBON SOLUTIONS OF ALKYLALUMINOXANE COMPOUNDS

BACKGROUND

This invention relates generally to hydrocarbon solutions of methylaluminoxane compounds and more specifically to such solutions which contain a straight chain trialkylaluminum compound which improves the solubility of the methylaluminoxane so as to permit the preparation of stable, colorless solutions.

Hydrocarbylaluminoxanes complexed with transition metal compounds have been found to be very effective olefin polymerization catalysts (Manzik et al. U.S. Pat. No. 3,242,099). Methylaluminoxane is an especially effective catalyst component. However, it has poor solubility in aliphatic hydrocarbon solvents which are preferred catalyst solvents because they are less toxic than aromatic hydrocarbons. Manufacturers of polymers which may come in contact with foodstuffs are concerned about solvent residues in their products and therefore seek to avoid the use of aromatic solvents during polymer production. Even in aromatic solvents, methylaluminoxane is not completely soluble such that the solutions become cloudy upon standing. Japanese application 63-87717 discloses the use of branched chain alkylaluminum compounds to improve solubility. Branched chain alkyl groups are known to have enhanced solubility in hydrocarbon solvents compared to straight-chain alkyl groups.

Surprisingly, we have found that clear solutions of methylaluminoxane (MAO) compositions in hydrocarbon solvents and especially in aliphatic hydrocarbon solvents can be prepared by dissolving methylaluminoxane and a straight chain trialkylaluminum compound which contains as few as two carbons per alkyl group, i.e. the readily available triethylaluminum (TEA), as well as higher alkyl groups such as tri-n-octylaluminum, in the solvent. Use of this latter compound permits the preparation of aromatic hydrocarbon free, clear solutions while adding only a fraction of aluminum values to the mixture (aluminum alkyl to aluminoxane aluminum mole ratios of about 1:10 or less). This provides a more economical solution to the methylaluminoxane solubility problem and minimizes the amount of aluminum residual in the polymers derived from these catalyst systems.

Further, we have found that adding straight chain trialkylaluminum compounds can also improve the clarity of aromatic solutions of methylaluminoxanes. Such solutions although initially clear, tend to form gels or particulates upon standing.

BRIEF SUMMARY

In accordance with this invention there is provided a hydrocarbon solvent solution of alkylaluminoxane comprising a hydrocarbon solvent having dissolved therein methylaluminoxane and an effective amount to solubilize said methylaluminoxane in said solvent of a tri-n-alkylaluminum wherein the alkyl groups each contain at least two carbon atoms.

DETAILED DESCRIPTION

Methylaluminoxane may exist in the form of a linear or cyclic polymer with the simplest component being tetramethylaluminoxane, $(CH_3)_2AlOAl(CH_3)_2$. The compounds preferred for use in olefin polymerization usually contain about 5 to 20 of the repeating units.

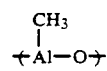

The compounds can be made, as is known in the art, by partial hydrolysis of trimethylaluminum (TMA) which is slurried or dissolved in an organic solvent such as toluene and treated with free water or a hydrated compound. The resulting methylaluminoxane product is usually a mixture of methyl aluminoxane and trimethylaluminum. The product is typically a solid which can be recovered from the reaction mixture by removal of the solvent.

The tri-n-alkylaluminum solubilizing agents for the methylaluminoxane are straight chain aluminum alkyls in which each alkyl group contains from 2 to about 20 carbon atoms. Alkylaluminum compounds having different alkyl groups can be used as well as mixtures of alkylaluminum compounds. Examples of suitable trialkylaluminum compounds include: triethylaluminum, tri-n-propylaluminum, tri-n-butylaluminum, tri-n-hexylaluminum, tri-n-octylaluminum, tri-n-decylaluminum, tri-n-dodecylaluminum, and the like. The mechanism of solubilization is not known but is believed to include partial alkyl group exchange with the methylaluminoxane. By using a higher alkyl aluminum compound such as tri-n-octylaluminum as a solubilzing agent, an aliphatic solvent soluble product having a relatively high 10:1 mole ratio of methylaluminoxane to trialkylaluminum content can be prepared.

Aliphatic hydrocarbons which can be used as solvents include, for example, pentane, hexane, heptane, octane, decane, dodecane, hexadecane, octadecane and the like with those having carbon numbers of 5 to 10 being preferred. Aromatic hydrocarbons which can be used as solvents include benzene, toluene, xylene, cumene and the like with those having carbon numbers of 6 to 20 being preferred.

The concentration of methylaluminoxane in the solutions of the invention can vary and generally ranges from about 5 to 30 weight percent of aluminum as methylaluminoxane product, based on the total weight of solution, in aromatic solvents and from about 5 to 15 weight percent in aliphatic solvents. Of this amount up to about 70 weight percent of the aluminum, and usually about 25 to 30 weight percent, may be present as trimethylaluminum.

The amount of tri-n-alkylaluminum which is effective to solubilize the methylaluminoxane will depend upon the tri-n-alkylaluminum compound. Generally, in aliphatic solvents from about 0.5 to 20 and preferably 1.0 to 10 moles of methylaluminoxane, calculated from the neat methylaluminoxane content of the methylaluminoxane product to be dissolved, can be solubilized per mole of tri-n-alkylaluminum (mole ratio of aluminum as aluminoxane to aluminum as tri-n-alkylaluminum of about 0.5:1 to 20:1) and in aromatic solvents from about 1 to 35 moles of methylaluminoxane can be solubilized per mole of tri-n-alkylaluminum.

The methylaluminoxane solutions of the invention retain the catalytic properties of the methylaluminoxane and show high activity as olefin polymerization catalyst components.

The solutions of the invention can be formed, for example, by mixing a hydrocarbon slurry of solid methylaluminoxane with tri-n-alkylaluminum or by adding solid methylaluminoxane to a hydrocarbon solution of the tri-n-alkylaluminum while using normal procedures for handling air-sensitive pyrophoric organic aluminum compounds. The mixing is conveniently done at ambient temperatures but temperatures of up to about 100° C. are suitable. Preferred temperatures are in the range of about 25° to 60° C.

In a novel and especially useful method of forming an aliphatic hydrocarbon solvent solution of methylaluminoxane having excellent catalytic activity, the tri-n-alkylaluminum is added to a crude methylaluminoxane product, which has been formed by the hydrolysis of trimethylaluminum in an aromatic solvent such as toluene, prior to removal of the solvent. The resulting mixture is concentrated by vacuum evaporation or by distillation to remove the solvent and much of the trimethylaluminum. The residual product oil is then dissolved in an aliphatic hydrocarbon solvent. This procedure avoids the need to isolate solid methylaluminoxane which is generally formed when the tri-n-alkylaluminum is not used, and the product oil is readily soluble in aliphatic solvents. Furthermore, the methylaluminoxane product solution is a very active polymerization catalyst component. The trimethylaluminum removed during the concentration process can be recycled to form additional methylaluminoxane.

The invention is further illustrated by, but is not intended to be limited to, the following examples.

EXAMPLE 1

To a 100 mL round bottom flask were added 2.0 grams of solid methylaluminoxane (42.5 wt % aluminum). This methyaluminoxane contained about 25 wt % trimethylaluminum (TMA). The methylaluminoxane was added to about 40 mL of dry heptane. The resulting slurry was stirred and triethylaluminum (22.9 wt % aluminum) was slowly added until a clear solution was obtained. The total weight of triethylaluminum added was 3.7 grams (0.84 gram aluminum). The final methylaluminoxane/triethylaluminum/heptane solution weighed 32.5 grams. Analysis of the clear product solution indicated that it contained 5.2 wt % aluminum. The mole ratio methylaluminoxane:triethylaluminum was 1:1 (i.e. 50% of the aluminum value was methylaluminoxane/trimethylaluminum and the remaining 50% was the added triethylaluminum). This modified methylaluminoxane/heptane solution showed high activity in an ethylene polymerization test (95.6 grams polymer were produced).

The ethylene polymerization test procedure uses a catalyst combination consisting of methylaluminoxane and bis(cyclopentadienyl)zirconium dichloride ($Cp_2ZrCl_2$) In the test 750 mL of dry toluene, is charged to a one liter autoclave which has been heated and purged with nitrogen for at least one hour. The methylaluminoxane/triethylaluminum /heptane solution (containing 8.3 m moles aluminum) is then added and the system heated to 80° C. A freshly prepared solution of $Cp_2ZrCl_2$ containing 0.03 m moles of $Cp_2ZrCl_2$ in toluene is then added and the reactor pressurized to 60 psig with ethylene. The ethylene polymerization is then conducted for a 10 minute period after which the polyethylene produced is collected by filtration, dried and weighed.

EXAMPLE 2

To a 100 ML round bottom flask containing about 40 ml of dry heptane were added 2.0 grams of solid methylaluminoxane (42.5 wt % Al). The mixture, containing undissolved methylaluminoxane was stirred and tri-n-octylaluminum (TNOA) (7.45 wt % aluminum) was slowly added to the methylaluminoxane/heptane slurry until a clear solution was obtained. The total weight of tri-n-octylaluminum added was 1.95 grams (equivalent to 0.14 gram of aluminum). The resulting methylaluminoxane/tri-n-octylaluminum/heptane solution weighed 30.3 grams. Analysis of the clear solution indicated it contained 3.2 wt % aluminum. The methylaluminoxane:tri-n-octylaluminum mole ratio was 6:1 (i.e. 82% of the aluminum value was methylaluminoxane/trimethylaluminum and the remaining 18% was the added tri-n-octylaluminum). This modified methylaluminoxane/heptane solution showed high activity in the ethylene polymerization test (99 grams polymer were produced).

EXAMPLE 3

To a 500 mL round bottom flask containing 400 mL of dry heptane were added 50.3 grams of solid methylaluminoxane, which contained some trimethylaluminum. The mixture was heated and allowed to reflux under a nitrogen atmosphere for about eight hours. After the solution was cooled, the solution was filtered through a 10–15 filter to remove the residual insoluble methylaluminoxane of which 17.5 grams was collected on the filter. The methylaluminoxane/heptane filtrate solution weighed 327.9 grams and contained about 65% of the original solid methylaluminoxane. Analysis of the solution (3.85 wt % aluminum) indicated that it contained 7.5 wt % methylaluminoxane, 2.5 wt % trimethylaluminum and upon hydroysis exhibited a gas/aluminum ratio of 1.6 The solution became cloudy with solids settling out after several days.

A 59.0 gram portion of this methylaluminoxane/heptane solution was added to a 100 mL round bottom flask. The methylaluminoxane solution was semi-clear with some solids present. To improve the solubility of the methylaluminoxane in the heptane solution, tri-n-octylaluminum was slowly added until a soluble, clear solution was obtained. The total weight of tri-n-octylaluminum added was 3.6 grams (equivalent 0.27 gram aluminum). Analysis of the solution indicated 4.1 wt % aluminum (3.6 wt % aluminum a methylaluminoxane/trimethylaluminum and only 0.43 wt % aluminum as tri-n-octylaluminum). This result corresponds to a methylaluminoxane:tri-n-octylaluminum mole ratio of about 9:1. The modified methylaluminoxane solution in the ethylene polymerization test provided 95 grams of polymer.

TABLE I

| | Methylaluminoxane/ALUMINUM ALKYL (TEA & TNOA)/HEPTANE SOLUTIONS | | | | |
|---|---|---|---|---|---|
| Example | Wt % Al (total) | Wt % Al as MAO[a] | Wt % Al as TNOA | Al Mole Ratio (MAO:TNOA) | Ethylene Polymerization Activity |
| 1 | 5.20 | 2.61 | 2.59[b] | 1:1[b] | 95.6 |
| 2 | 3.18 | 2.74 | 0.44 | 6:1 | 99.2 |

TABLE I-continued

Methylaluminoxane/ALUMINUM ALKYL (TEA & TNOA)/HEPTANE SOLUTIONS

| Example | Wt % Al (total) | Wt % Al as MAO[a] | Wt % Al as TNOA | Al Mole Ratio (MAO:TNOA) | Ethylene Polymerization Activity |
|---|---|---|---|---|---|
| 3 | 4.09 | 3.68 | 0.41 | 9:1 | 95.0 |

[a] Al content of MAO also contains some Al as TMA.
[b] TEA added to the MAO/heptane solution instead of TNOA.

EXAMPLE 4

To a one liter round bottom flask were added 161 grams of a 27.3 wt % methylaluminoxane/toluene solution. This methylaluminoxane solution was then diluted to a 10 wt % methylaluminoxane solution with the addition of 274 grams of toluene. The resulting methylaluminoxane/toluene solution was still cloudy. Upon adding 8.3 g of tri-n-octylaluminum at room temperature and thoroughly mixing, the solution became clear. The methylaluminoxane:tri-n-octylaluminum mole ratio was 35:1.

EXAMPLE 5

To a one liter round bottom flask were added 450 grams of a crude methylaluminoxane/toluene solution (2.0 wt % aluminum; 30:70 methylaluminoxane:trimethylaluminum mole ratio. This solution was stirred and 13.3 grams of tri-n-octyl aluminum (9:1 methylaluminoxane plus trimethylaluminum:tri-n-octylaluminum mole ratio) were slowly added. The solution was then stripped at 50° C. under vacuum to remove the toluene and some trimethylaluminum such that 23.3 grams of an oily material remained in the flask. The oily product was dissolved in 100 grams of dry heptane to give a clear solution containing no gels or solids. Analysis of the solution indicated it contained 4.2 wt % aluminum with a methylaluminoxane:tri-n-octylaluminum plus trimethylaluminum mole ratio of 3:2. This modified methylaluminoxane/heptane solution showed high activity in the ethylene polymerization test (90 grams polymer). The process of Example 5 was repeated using different total batch size and about a 10:1 methylaluminoxane plus trimethylaluminum:tri-noctylaluminum mole ratio. The product had a very high polymerization activity (150-170 grams of polymer were produced).

What is claimed is:

1. A hydrocarbon solvent solution of alkylaluminoxane comprising methylaluminoxane and an effective amount to solubilize said methylaluminoxane in said solvent of a tri-n-alkyl aluminum wherein the alkyl groups each contain at least two carbon atoms.

2. The solution of claim 1 wherein said hydrocarbon solvent is an aliphatic hydrocarbon.

3. The solution of claim 2 wherein said aliphatic hydrocarbon contains from 5 to 20 carbon atoms, the solution contains from about 5 to 15 wt percent aluminum as methylaluminoxane product, and the mole ratio of aluminum as methylaluminoxane to aluminum as tri-n-alkylaluminum is from about 0.5:1 to 20:1.

4. The solution of claim 3 wherein the alkyl groups of said tri-n-alkylaluminum each contain from 2 to about 20 carbon atoms.

5. The solution of claim 3 wherein said tri-n-alkylaluminum is triethylaluminum.

6. The solution of claim 3 wherein said tri-n-alkylaluminum is tri-n-octylaluminum.

7. The solution of claim 3 wherein the mole ratio of aluminum as methylaluminoxane to aluminum as tri-n-alkylaluminum is from about 1:1 to 10:1.

8. The solution of claim 3 wherein said solvent is selected from pentane, isopentane, hexane and n-heptane.

9. The solution of claim 7 wherein said solvent is selected from pentane, isopentane, hexane and n-heptane 10. The solution of claim 1 wherein said solvent is an aromatic solvent.

11. The solution of claim 10 wherein the aromatic hydrocarbon contains from about 6 to 20 carbon atoms, the solution contains from about 5 to 30 wt. percent aluminum as methylaluminoxane product, and the mole ratio of aluminum as methylaluminoxane to aluminum as tri-n-alkylaluminum is from about 1:1 to 35:1.

12. The solution of claim 11 wherein the alkyl groups of said tri-n-alkylaluminum contain from 2 to 20 carbon atoms.

13. The solution of claim 11 wherein such solvent is selected from benzene, toluene, xylene and cumene.

14. A process for making an aliphatic hydrocarbon solvent solution of alkylaluminoxane comprising the steps of:
  (a) hydrolyzing trimethylaluminum in an aromatic solvent to form a crude methylaluminoxane product,
  (b) dissolving a tri-n-alkylaluminum compound, wherein the alkyl groups each contain at least 2 carbon atoms, in the aromatic solvent which contains said crude methylaluminoxane product,
  (c) removing said aromatic solvent from the mixture formed in step (b), and
  (d) dissolving the residue of step (c) in an aliphatic hydrocarbon solvent.

15. The process of claim 14 wherein said aliphatic hydrocarbon solvent contains from 5 to 20 carbon atoms, said solution contains from about 5 to 15 wt. percent aluminum as methylaluminoxane product and the mole ratio of aluminum as methylaluminoxane to aluminum as tri-n-alkylaluminum is from about 0.5:1 to 20:1.

16. The process of claim 14 wherein the alkyl groups of said tri-n-alkylaluminum each contain from 2 to about 20 carbon atoms.

17. The process of claim 14 wherein said tri-n-alkylaluminum is triethylaluminum.

18. The process of claim 14 wherein said tri-n-alkylaluminum is tri-n-octylaluminum.

19. The process of claim 14 wherein unhydrolyzed trimethylaluminum is removed in step (c).

* * * * *